United States Patent [19]
Kolbe et al.

[11] Patent Number: 4,703,273
[45] Date of Patent: Oct. 27, 1987

[54] 140 GHZ PULSED FOURIER TRANSFORM MICROWAVE SPECTROMETER

[75] Inventors: William F. Kolbe, Oakland; Branko Leskovar, Moraga, both of Calif.

[73] Assignee: The United States of America as represented by the United States Department of Energy, Washington, D.C.

[21] Appl. No.: 759,783

[22] Filed: Jul. 29, 1985

[51] Int. Cl.$^4$ .............................. G01N 27/78
[52] U.S. Cl. .................... 324/314; 324/309; 324/58.5 C; 332/10
[58] Field of Search .................... 332/53–56, 332/9 R, 9 T, 10; 324/307–309, 314–317, 58 C, 58.5 C, 57 PS, 57 Q

[56] References Cited
U.S. PATENT DOCUMENTS

| | | | |
|---|---|---|---|
| 2,429,683 | 10/1947 | Haantses | 332/55 |
| 2,457,673 | 12/1948 | Hershberger . | |
| 2,524,290 | 10/1958 | Hershberger . | |
| 2,602,835 | 7/1952 | Hershberger . | |
| 3,372,331 | 3/1968 | Larson . | |
| 3,456,185 | 7/1969 | Akao . | |
| 3,582,778 | 6/1971 | Faulkner . | |
| 3,691,453 | 9/1972 | Rupp . | |
| 3,691,454 | 9/1972 | Hrubesh . | |
| 3,714,550 | 1/1973 | Hyde . | |
| 3,798,532 | 3/1974 | Hauser . | |
| 4,214,202 | 7/1980 | Bonori | 324/314 |

OTHER PUBLICATIONS

Kolbe: "Sensitivity and Response Time Improvements in MM-Wave Spectrometer"–Rev. Sci. Instr.–Jun. 82–pp. 769-775.
Kolbe: "140 GHz Pulsed Fourier Tranform Spectrometer", Rev. Sci. Instr.–Jan. 85–pp. 97-102.

Primary Examiner—Reinhard J. Eisenzopf
Assistant Examiner—Jose M. Solis
Attorney, Agent, or Firm—Clifton E. Clouse, Jr.; Roger S. Gaither; Judson R. Hightower

[57] ABSTRACT

A high frequency energy pulsing system suitable for use in a pulsed microwave spectrometer (10), including means (11, 19) for generating a high frequency carrier signal, and means (12) for generating a low frequency modulating signal. The carrier signal is continuously fed to a modulator (20) and the modulating signal is fed through a pulse switch (23) to the modulator. When the pulse switch (23) is on, the modulator (20) will produce sideband signals above and below the carrier signal frequency. A frequency-responsive device (31) is tuned to one of the sideband signals and away from the carrier frequency so that the high frequency energization of the frequency-responsive device (31) is controlled by the pulse switch (23).

14 Claims, 5 Drawing Figures

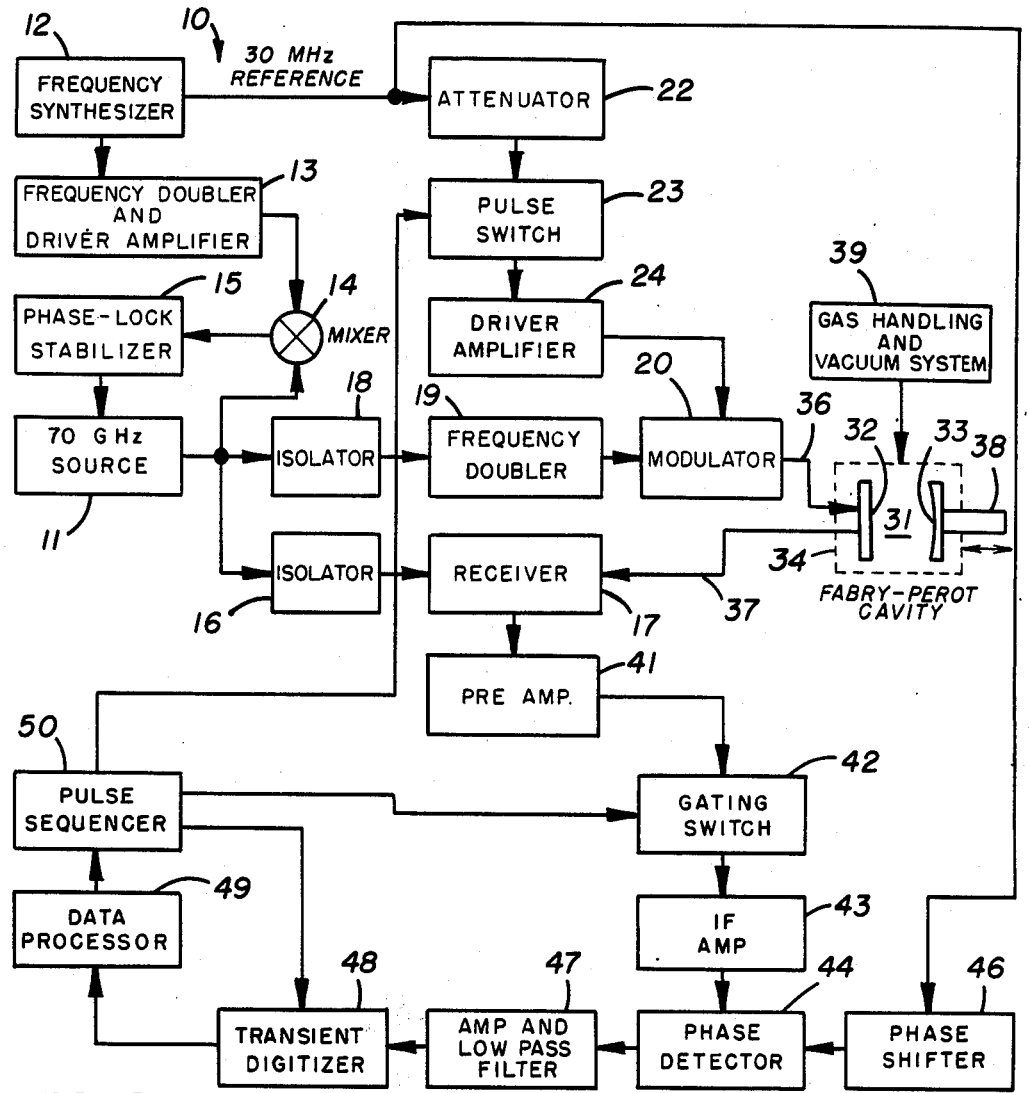
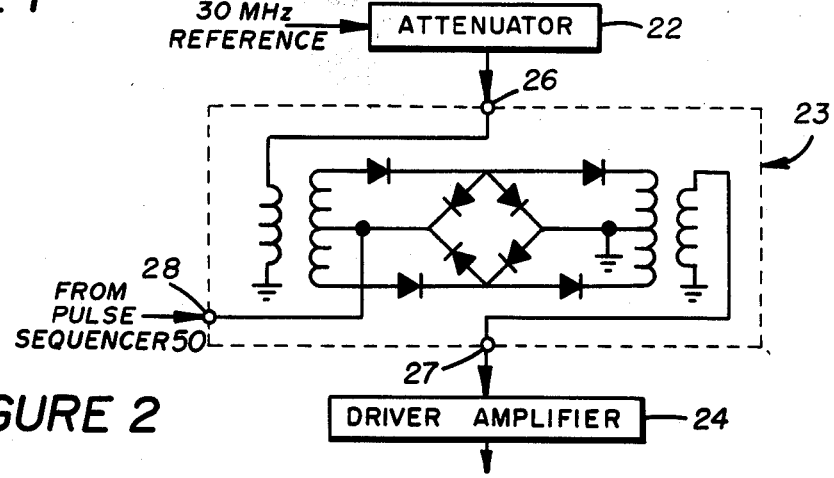
FIGURE 1
FIGURE 2

140 GHZ PULSED FOURIER TRANSFORM MICROWAVE SPECTROMETER

BACKGROUND OF THE INVENTION

This invention relates to a method and apparatus for generating pulses of high frequency energy and particularly to a pulsed microwave spectrometer. The United States Government has rights in this invention pursuant to Contract No. DE-AC03-76SF00098 between the U.S. Department of Energy and the University of California, Lawrence Berkeley Laboratory.

In contrast to steady-state microwave spectroscopy, in which molecular species are detected by their equilibrium absorption of microwave energy, pulsed Fourier transform spectroscopy exploits the transient polarization of the molecules produced by a brief pulse of microwave energy at a frequency in the vicinity of the transition. The polarized molecules emit a polarization decay signal at their resonance frequency, which is detected by a sensitive microwave receiver. The decay signals are then digitized and signal-averaged to enchance the signal-to-noise ratio. Subsequently, the time domain signal can be Fourier transformed to obtain the resonance line-shape. This method is directly analogous to that employed in pulsed nuclear magnetic resonance (NMR) experiments and has many of the advantages associated with that technique.

In recent years pulsed microwave spectrometers have been developed which have demonstrated the usefulness of pulsed Fourier transform spectroscopy. However, these spectrometers have, for the most part, been limited to operating frequencies of less than 18 GHz because of the unavailabilty of microwave switches suitable for forming the polarizing pulses. In general, the requirements for a suitable pulse forming switch includes an on/off ratio in the order of 90 dB or more and a risetime of a few nanoseconds.

Commercial pin diode switches are currently availabe with on/off ratios of up to 60 dB for frequencies as high as 50 GHz. These units, however, have bandwidths of only a few percent, making them very expensive for spectroscopic applications. Wider bandwidth switches operating at frequencies of up to 110 GHz are available, but these switches have on/off ratios of less than 20 dB and are not suitable for such applications.

The frequencies of the stronger transistions of many gases are considerably higher that can be handled with present pulsed spectrometers. For example, a strong transistion of $SO_2$ in the vicinity of 140 GHz. Prior to the present invention, pulsed spectroscopy could not be carried out at such frequencies.

SUMMARY OF THE INVENTION

It is an object of the present invention to provide a method and apparatus for switching high frequency energy with a very high on/off ratio and a very fast risetime.

It is a further object of the invention to provide a method and apparatus for switching high frequency energy using a conventional low frequency switch.

A still further object of the invention is to provide a method and apparatus for switching high frequency energy which will enable pulsed spectroscopy to be carried out at transistion frequencies much higher than is possible with existing equipment.

Additional objects, advantages and novel features of the invention will be set forth in the description which follows, and in part will become apparent to those skilled in the art upon examinition of the following or may be learned from practice of the invention. The objects and advantages of the invention may be realized, and attained by means of the instrumentalities and combinations particularly pointed out in appended claims.

To achieve the foregoing and other objects, and in accordance with the present invention, as embodied and broadly described herein, a continuous high frequency carrier signal and a low frequency modulating signal are generated, with the low frequency modulating signal being fed through a switch to a modulator which modulates the high frequency carrier signal with the low frequency modulating signal to produce a modulated sideband signal above or below the frequency of the carrier signal. A high frequency responsive device is tuned to the sideband signal and away from the frequency of the carrier signal, and the device is pulsed by switching the modulating signal on and off.

BRIEF DESCRIPTION OF THE DRAWINGS

The accompanying drawings, which are incorporated in and form a part of the application and, together with the description, serve to explain the principles of the invention.

FIG. 1 is a block diagram of a pulsed microwave spectrometer made in accordance with the present invention.

FIG. 2 is a block and circuit diagram of the pulse switch portion of FIG. 1.

DESCRIPTION OF THE PREFERRED EMBODIMENT

Figure 3:
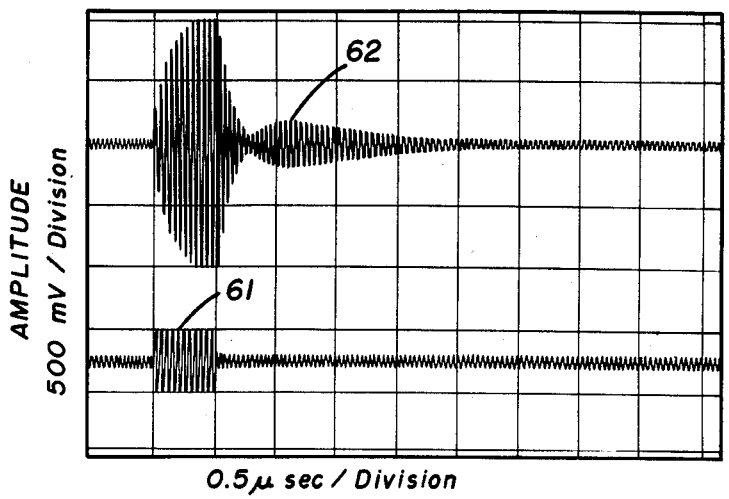
FIG. 3 is an illustration of the cavity excitation pulse and transient emission signal obtained with the system of FIG. 1, with a pulse width of 500 msec and gas pressure of 1.0 mTorr.

Referring now to the drawings, which illustrate a preferred embodiment of the invention, FIG. 1 illustrates a pulsed microwave spectrometer, generally represented by the reference numeral 10, constructed in accordance with the present invention. For purposes of explanation, the spectrometer 10 is shown as one operating to produce excitation pulses in the vicinity of 140 GHz, for the detection of transient emission signals using $SO_2$ gas as a sample species.

Microwave energy in the vicinity of 70 GHz is produced by the 70 GHz source 11, preferably a klystron, phase-locked to the frequency synthesizer 12 by the frequency doubler and amplifier 13, mixer 14 and phase-lock stabilizer 15.

Of the approximately 80 mW of power available from the source 11, ten percent is applied through isolator 16 to the receiver 17, where such power is used to provide local oscillator power for the receiver 17. The remainder of the power from source 11 is applied through isolator 18 to a tunable high efficiency frequency doubler 19 which generates a high frequency carrier signal in the vicinity of 140 GHz. The carrier signal is then modulated by modulator 20.

A 30 MHz reference signal from the frequency synthesizer 12 is used as a low frequency modulating signal, such modulating signal being fed through attenuator 22, pulse switch 23 and driver amplifier 24 to modulator 20.

With the pulse switch 23 closed to apply the modulating signal to modulator 20, the resulting signal from the modulator will consist of the 140 GHz carrier signal plus sideband signals 30 MHz above and below the carrier signal frequency.

For purposes of explanation, the frequency doubler 19 and modulator 20 have been shown as separate units. However, these units may be combined into a single modulated frequency double unit, such as a unit constructed in accordance to the design furnished by the National Radio Astronomy Observatory, and described by J. W. Archer in IEEE Trans. Microwave Theory Tech., MTT-29, p. 552 et seq. (1981). Such a modulated frequency doubler has a conversion efficiency of at least 15% over an output frequency range of 130 to 146 GHz. The frequency doubler is provided with an appropriate d.c. bias to maximize the output power and is modulated at 30 MHZ to produce a 140 GHz carrier signal with sidebands above and below the carrier. The maximum output power in each of the sidebands is greater than 1 mW.

The pulse switch 23 used in the particular system of FIG. 1 is a commercially available model S1 solid state switch manufactured by Watkins-Johnson, Palo Alto, Calif. and the schematic diagram of such pulse switch is shown in FIG. 2. The 30 MHz modulating signal from attenuator 22 is applied to the input port 26 of the pulse switch 23 and the output port 27 is connected to the driver amplifier 24. With this particular switch, which operates in the range of 0.5-500 MHz, a biasing current of +20 mA into the switch port 28 gives the on-condition, and −20 mA into that port will give the off-condition. With the Schottky barrier diodes in this switch, and operating at 30 MHz, the on-off ratio is greater than 90 dB and the maximum risetime is 1.0 nsec.

Returning to the system of FIG. 1, the output of the modulator 20 is fed to the tunable Fabry-Perot cavity 31, consisting of two opposing mirrors, 32 and 33, each 5 cm in diameter, one flat and the other spherical, mounted in a vacuum chamber 34. Two coupling waveguides, 36 and 37, are attached to the flat mirror 32 through coupling holes 4.0 mm apart and 0.7 mm in diameter. The spherical mirror 33 has a radius of curvature of 14.8 cm and is mounted in a semi-confocal configuration with a distance of about 7.4 cm between the two mirrors. The cavity can be tuned by moving the spherical mirror 33 with the use of a piezoelectric transducer and a stepping motor and micrometer drive, indicated generally at 38. The gas handling and vacuum system 39 maintains the desired low pressure in the cavity. The loaded Q of the cavity is about 73,000 and the transmission loss through the cavity is approximately 18 dB. By appropriately tuning the cavity to the desired value, either sideband can be detected. Because of the high Q of the cavity only one sideband signal from the modulator 20 passes through the cavity and reaches the receiver 17. The Fabry-Perot cavity 31 thus functions as a high frequency responsive device tuned to the frequency of one of the sideband signals and away from the frequency of the 140 GHz carrier signal.

After passing through the Fabry-Perot cavity the microwave signal is converted to an IF frequency of 30 MHz by the receiver 17. The receiver 17 shown herein includes a subharmonically pumped mixer to permit the 70 GHz source frequency be used as a local oscillator. Alternatively, a second frequency doubler and a fundamental mixer could be used. The 30 MHz IF signal passes through preamplifier 41, and then through a gating switch 42 to prevent saturation of the IF amplifier 43 during the polarization pulse from modulator 20. The amplified IF signal is then converted to baseband frequency by means of a phase detector 44 driven by the same 30 MHz reference signal used with the modulator 20. A phase shifter 46 is used to obtain the in-phase component of the cavity signal.

The detected signal passes through the amplifier and low pass filter 47 and is digitized in the transient digitizer 48. The digitizer used in the system of FIG. 1 has a maximum sampling rate of 20 MHz and a memory size of up to 8K channels. The digitized data is then fed to the data processor 49 which is used to average the digitized data from a number of pulse sequences and to further process the data. The data processor 49 also controls the pulse sequencer 50 that drives the pulse switch 23 and gating switch 42, and triggers the transient digitizer 48.

In order to illustrate the generation of transient emission signals, the cavity was filled with $SO_2$ gas at a pressure of a few mTorr. The microwave source was set so that one of the sideband signals from modulator 20 was 140.3062 GHz, corresponding to the 6(2,4)–6(1,5) transition of the gas, and the cavity was tuned to resonate at that frequency. The excitation pulse width was set to a convenient value in the order of 500 nsec and the 30 MHz modulation power was adjusted to maximize the amplitude of the emission signal.

FIG. 3 shows the cavity excitation pulse 61 at the input to the cavity 31 and the transient emission signal 62 at the output of the preamplifier 41, for a gas pressure of 7 mTorr and a pulse width of 500 nsec. Altough the rectangular input pulse shown in signal 62 is distorted by the cavity time constant, it is known that the polarization produced is proportional to the integral of the pulse to first order independent of this distortion. In order that the molecular emission signal be observed, the cavity decay time must be short compared to the molecular relaxation time. In the presently described system, the cavity decay time is in the order of 175 nsec.

In order to display the transient emission signal, the output of the receiver was amplified, phase detected and digitized, as described above.

Figure 4:
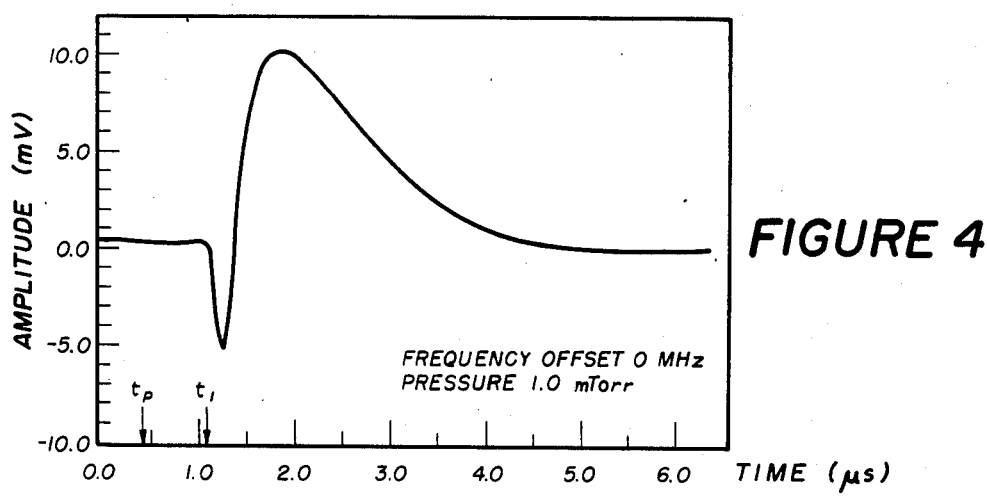
FIG. 4 illustrates the transient emission signal obtained with the system of FIG. 1, calculated from an average of 1,000 scans taken at a gas pressure of 1.0 mTorr.

FIG. 4 shows the results for an average of 1,000 scans taken at a pressure of 1.0 mTorr. The excitation pulse begins at T=0 and, as shown in the FIG., extends for 400 nsec (i.e. at $t_p$). A short time later, at $t_1$, the receiver gating signal is turned off, permitting the tail of the cavity decay and the oppositely phased emission signal to be observed.

In FIG. 4, the excitation frequency has been chosen to correspond exactly to the rotational transition frequency. If the frequency is shifted by 2 MHz, the emission signal will appear, as in FIG. 5, as a damped sinewave of that frequency. In either case, the lineshape in the frequency domain can be recovered by Fourier transformation.

Figure 5:
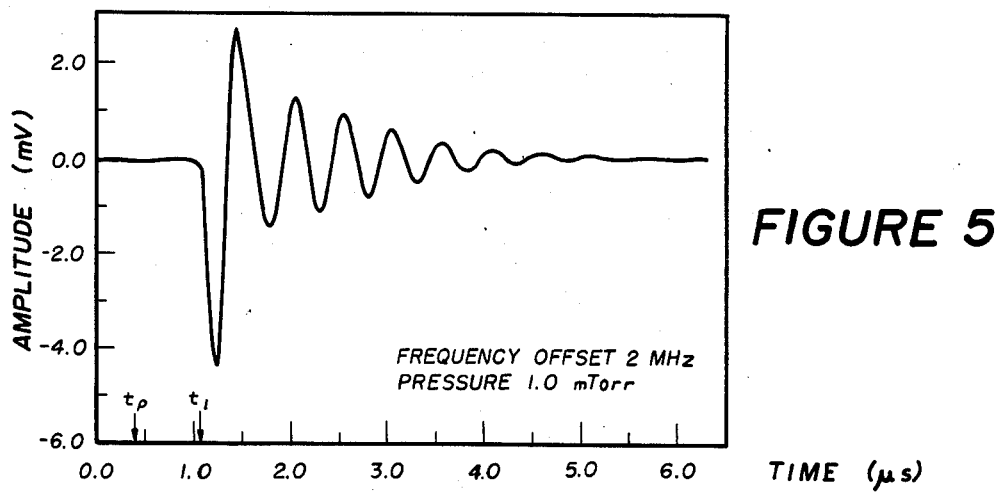
FIG. 5 is a calculated transient emission signal obtained with the system of FIG. 1, but with a frequency offset of 2.0 MHz.

The results obtained from the above described system and illustrated in FIGS. 3–5 clearly demonstrate that the pulsing system of the present invention provides a very satisfactory manner of switching high frequency energy in pulsed microwave spectrometer at frequencies much higher than has been heretofore possible.

The foregoing description of the preferred embodiment has been presented for purposes of illustration and description. The embodiment was chosen in order to explain most clearly the principles of the invention and a practical application thereof, thereby to enable others in the art to utilize most effectively the invention in different embodiments and with various modifications as are suited to the particular use contemplated. In particular, the foregoing description is not intended to be exhaustive or to limit the invention to the precise form, since many modifications and variations are possible in light of the invention. For example, although the description relates specifically to a pulsed microwave spectrometer, the invention can have utility in other systems wherein high frequency energy is to be switched on and off. Also, although the present description discloses a Fabry-Perot cavity as being the frequency responsive device to which the pulsed energy is applied, other frequency responsive devices could be used in carrying out the invention. For example, a high Q filter, tuned to one of the sidebands and away from the carrier frequency could function as a frequency responsive device and allow pulses of sideband energy to pass through the filter to a further circuit element. It is intended that the scope of the invention be defined by the claims appended hereto.

What is claimed is:

1. A method of pulsing a high frequency responsive device with high frequency energy comprising:
   (a) generating a continuous high frequency carrier signal,
   (b) periodically modulating said high frequency carrier with a low frequency modulating signal to produce a modulated sideband signal above or below the frequency of said carrier signal,
   (c) tuning said high frequency responsive device to the frequency of said sideband signal and away from the frequency of said carrier signal.

2. A method of pulsing a high frequency responsive device with high frequency energy as set forth in claim 1, wherein the modulating step (b) includes:
   (b1) continuously generating said low frequency modulating signal,
   (b2) applying said modulating signal through a switch to a modulator wherein said carrier signal is modulated by said modulating signal,
   (b3) periodically closing and opening said switch.

3. A method of pulsing a high frequency repsonsive device with high frequency energy as set forth in claim 2 wherein the frequency of said carrier signal is above 20 Gigahertz.

4. A method of pulsing a high frequency responsive device with high frequency energy as set forth in claim 3 wherein said switch has an on/off ratio of at least 90 dB.

5. A method of pulsing a high frequency responsive device with high frequency energy as set forth in claim 4 wherein said high frequency responsive device is a tunable Fabry-Perot cavity.

6. A high frequency pulsed system comprising:
   (a) means for generating a continuous high frequency carrier signal,
   (b) modulating means for periodically modulating said high frequency carrier signal with a low frequency modulating signal to produce a modulated sideband signal above or below the frequency of said carrier signal,
   (c) a high frequency responsive device tuned to the frequency of said sideband signal and away from the frequency of said carrier signal.

7. A high frequency pulsed system as set forth in claim 6, wherein said modulating means (b) includes:
   (b1) low frequency signal generator means for continuously generating said low frequency modulating signal.
   (b2) a modulator for modulating said carrier signal by said modulating signal,
   (b3) switch means between said low frequency generator means and said modulator for applying said modulating signal from said low frequency generator means to said modulator,
   (b4) means for closing and opening said switch means.

8. A high frequency pulsed system as set forth in claim 7 wherein said switch has an on/off ratio of at least 90 dB.

9. A high frequency pulsed system as set forth in claim 7, wherein said means for generating said carrier signal generates a carrier signal higher than 20 Gigahertz.

10. A high frequency pulsed system as set forth in claim 9, wherein said switch has an on/off ratio of at least 90 dB.

11. A pulsed microwave spectrometer system including:
    (a) means for continuously generating a high frequency carrier signal,
    (b) means for continuously generating a low frequency modulating signal,
    (c) a modulator for modulating said carrier signal to produce sideband signals above and below the frequency of said carrier signal,
    (d) switch means for applying said modulating signal from said means for generating the modulating signal to said modulator,
    (e) means for closing and then opening said switch means,
    (f) A Fabry-Perot cavity connected to said modulator and tuned to the frequency of one of said sideband signals.

12. A pulsed microwave spectrometer system as set forth in claim 11, wherein the frequency of said carrier signal is above 20 Gigahertz.

13. A pulsed microwave spectrometer system as set forth in claim 11 wherein the frequency of said carrier signal is in the order of 140 Gigahertz and the frequency of said modulation signal is in the order of 30 Megahertz.

14. A pulsed microwave spectrometer system as set forth in claim 13 wherein said switch has an on/off ratio of at least 90 dB.

* * * * *